United States Patent [19]

Szelke et al.

[11] Patent Number: 4,772,686

[45] Date of Patent: Sep. 20, 1988

[54] ENZYME INHIBITION

[75] Inventors: Michael Szelke, Ruislip; David M. Jones, Hayes, both of England

[73] Assignee: Aktiebolaget Hassle, Mohndal, Sweden

[21] Appl. No.: 1,851

[22] Filed: Jan. 9, 1987

[30] Foreign Application Priority Data

Mar. 4, 1983 [GB] United Kingdom ............... 83 05985

[51] Int. Cl.$^4$ .............................................. C07K 5/08
[52] U.S. Cl. .................................................. 530/331
[58] Field of Search ................... 530/332, 331; 514/18

[56] References Cited

U.S. PATENT DOCUMENTS 4,629,724 12/1986 Ryono et al. ..................... 514/18
4,638,047 1/1987 Szelke et al. ..................... 530/332

Primary Examiner—Delbert R. Phillips
Attorney, Agent, or Firm—Larson and Taylor

[57] ABSTRACT

Peptides wherein an amide bond is replaced by nonhydrolyzable isosteric linkage are disclosed as thrombogenic inhibitors.

5 Claims, No Drawings

ENZYME INHIBITION

This is a continuation of application Ser. No. 668,277, filed Oct. 31, 1984, now U.S. Pat. No. 4,638,047.

The invention relates to peptide analogues and to the inhibition of thrombogenesis.

THROMBOGENESIS

Blood clotting depends on a complex series of actions leading finally to cleavage of fibrin from circulating fibrinogen by the protease thrombin, and its subsequent cross linking to form a stable structure. Thrombin production falls in two parts, an 'intrinsic' system based on circulating blood components and an 'extrinsic' system requiring tissue components. In each, there is a cascade of reactions, a series of inactive 'factors' each being converted by proteolytic reaction into the corresponding 'a' factor that is itself a proteolytic enzyme effecting the next step.

In the intrinsic system the actions start with circulating Hageman factor (factor XII) undergoing contact activation, becoming bound to damaged surfaces or platelet aggregations. A peptide is cleaved from it by the circulating protease kallikrein, forming factor XIIa. Factor XIIa in the presence of circulating high molecular weight kininogen (MMW-K) then a) cleaves circulating plasma thromboplastin antecedent (factor XI) to give plasma thromboplastin (factor XIa) itself and b) cleaves circulating pre-kallikrein (Pre-K, Fletcher factor) giving more kallikrein and thus a self-accelerating action. Plasma thromboplastin, in the presence of calcium ions, cleaves circulating Christmas factor (factor IX) to give factor IXa. Factor IXa, with circulating antihaemophilic globulin (AHG, factor VIII) and in the presence of calcium ions and phospholipid micelles from platelets, forms a lipoprotein complex with circulating Stuart factor (factor X) and cleaves it to form factor Xa. Finally factor Xa, with circulating labile factor (factor V) and in the presence of calcium ions and phospholipid micelles, forms a lipoprotein complex with prothrombin (factor II) and cleaves it to form thrombin (factor IIa) itself.

In the extrinsic system, a serum glyco-protein proconvertin (factor VII) is cleaved by several proteases from the intrinsic system (factors XIa and XIIa and kallikrein) to form factor VIIa. Factor VIIa, with a tissue lipoprotein called tissue thromboplastin (factor III), and in the presence of calcium ions, forms a complex with further circulating factor X and cleaves it to form a second source of factor Xa, enhancing thrombin production.

Finally, thrombin from both sources converts circulating fibrinogen to the soluble form of fibrin, which spontaneously polymerizes into filaments and is then cross linked under the action of an enzyme (factor XIIIa) formed, by a second action of thrombin, from circulating fibrin stabilising factor (factor XIII).

In tabular form the accelerating cascade of actions is:

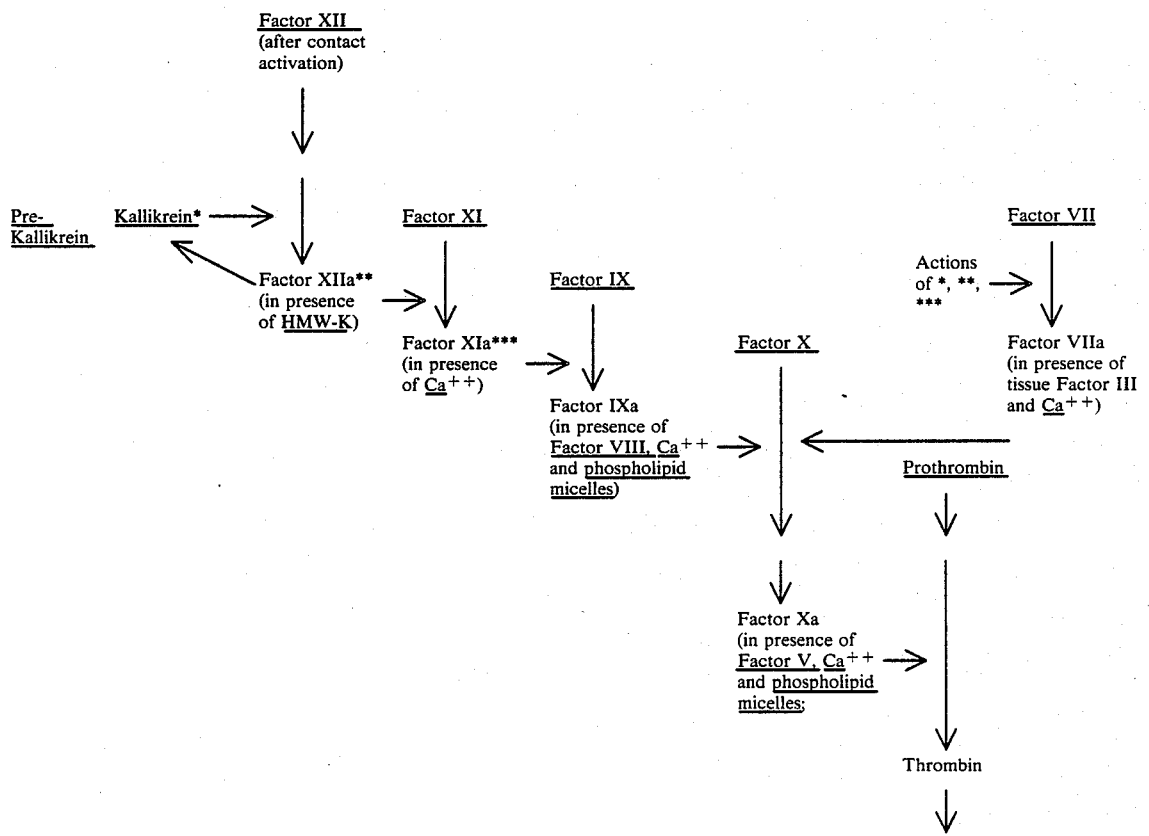

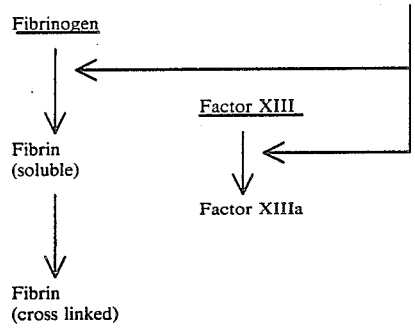

Notes
(i) Materials circulating in blood underlined (ii) Arrows A ⟶ B ↓ C   show conversion of B to C by A, the presence of other necessary materials being stated.

(iii) HMW-K = high molecular weight kininogen

THROMBIN

Specifically, thrombin acts on the A α-chain of fibrinogen

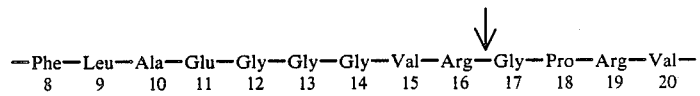

—Phe—Leu—Ala—Glu—Gly—Gly—Gly—Val—Arg—Gly—Pro—Arg—Val—
  8    9   10   11   12  13  14   15  16   17  18   19  20

Besides its central action in fibrin clot formation set out above, thrombin is a key factor in the platelet aggregation state of thrombogenesis as discussed for example in H. J. Weiss "Platelets: Pathophysiology and Antiplatelet Drug Therapy" Ch. 1 (Liss, New York, 1982) or D. Ogsten and B. Bennett (Eds.) "Haemostasis: Biochemistry, Physiology and Pathology" Ch. 13 (Wiley, 1977). The details are not fully understood, but thrombin is the strongest inducer of the 'platelet reaction' (shape change, aggregation, dense granule and α-granule secretion) responsible for primary haemostasis. The action of thrombin is preceded by its interaction with a specific binding protein in the platelet membrane, and the inhibitors of the present invention also appear to interfere with this binding.

Specific inhibitors of thrombin are thus to be expected to act as highly effectively antithrombotic agents and/or anticoagulants, giving alternatives to existing therapeutic and prophylactic agents. Heparin is for example widely used against thrombosis, but it carries a high risk of haemorrhage, is ineffective in many conditions, and gives a variable response from patient to patient and from time to time in a given patient so that careful monitoring is required. Oral anticoagulants also, used particularly for prophylaxis and control of venous thrombosis, take time to develop their effect and are interfered with by many other drugs. The inhibitors of the present invention act at once, and because of their specificity and chemical nature may be expected to be without side effects or drug interactions. Further, by acting only on the thrombin trigger to platelet aggregation, they leave the collagen trigger available to preserve haemostasis. Administration is simple, for example intranasal.

SUBSTRATE STRUCTURE

It is known that most of the affinity sites for thrombin are present in the N-terminal (8-20) fragment of fibrinogen, and that partial sequences of this region bind tightly to the enzyme and are rapidly hydrolysed by it. between $Arg^{16}$ and $Gly^{17}$, to remove the N-terminal hexadecapeptide fragment (fibrinopeptide A). Subsequently, cleavage between residues $Arg^{19}$ and $Val^{20}$, again by thrombin, takes place at a much slower rate, releasing a further tripeptide fragment. The enzyme also removes the N-terminal tetradecapeptide fragment (fibrinopeptide B) of the fibrinogen Bβ chain by slow hydrolysis between $Arg^{14}$ and $Gly^{15}$. This release of the fibrinopeptides from fibrinogen is followed by polymerisation of the resulting fibrin monomer to form "soluble" fibrin. The latter is then converted into stable, "insoluble" fibrin gel by factor XIIIa, which cross links two α or γ-chains of neighbouring fibrin molecules by transamidation.

THE INVENTION

The present invention is based on partial sequences of human fibrinogen, which possess high binding affinity for thrombin. These substrate fragments are modified by replacement of the Scissile peptide bond —CO—NH— (i.e. the bond normally cleaved by thrombin) with a non-hydrolysable isosteric linkage (e.g. a keto —CO—CH$_2$—, hydroxy —CH(OH)—CH$_2$ or reduced —CH$_2$—NH— linkage).

Optionally, other positions of the substrate sequence are also modified to provide increased binding affinity, e.g. by introducing DPhe at position 14 and/or Pro at position 15 of fibrinogen, as previously proposed in itself by M. Pozsgay et al. Eur. J. Biochem 115 941 (1981), or increased metabolic stability, e.g. by isosteric substitution of additional peptide linkages or by protection of the N-terminus and/or C-terminus with suitable protecting groups.

General reference to amino acids and amino acyl residues and side-chains in both the description and claims, is to be taken as reference to such whether naturally occurring in proteins or not, and to both D- and L-forms; and amino acid is to be taken as including imino acid. All asymmetric centres may be of either R or S configuration unless stated otherwise.

The compounds of the present invention, showing desirable anti-thrombolic or anti-coagulant action, are of the general formula I below (wherein numbering of residues corresponds to that in human fibrinogen, but without limitation of the invention):

$$X-Y-Z-A-Pro-Arg-B-W \qquad (I)$$
$$\phantom{X-Y-Z-}14\phantom{-}15\,16,17\phantom{-}18\phantom{--}19\phantom{-}20$$

wherein X and W are terminal groups optionally including further amino acyl groups; Y where present is glycine phenylalanine or other lipophilic amino acid residue; Z is glycine N-methyl alanine valine proline or a ring homologue of proline; A is a 'hydroxy' 'reduced' or preferably 'keto' dipeptide analogue residue of which the first residue is either arginine or has the side chain terminal amidino group of arginine and the second is a glycine alanine or related residue with a hydrocarbon side chain optionally hydroxy terminated; Arg or Pro and Arg where present are optionally substituted; and B where present is valine proline or a group —NH—$(CH_2)_n$—CO— (n=0-5), or with W represents an aminoalcohol; and wherein optionally the terminal groups are linked to give a cyclic structure.

In more detail, in formula I desirably:

X—H or a protective group including lower alkyl ($C_1$-$C_5$), or lower aliphatic acyl ($C_1$-$C_5$), or aromatic acyl, e.g. Ar—$(CH_2)_n$—CO— or Ar—O—$(CH_2)_n$—CO— where n=0-2 and Ar is phenyl or other (including mono- or bicyclic) aromatic group which may be substituted especially mono-substituted with one of the following groups, preferably (when phenyl) in the 2- or 4-position:
F, Cl, Br, I, —$CF_3$, —OH, —OR or —R (R=$C_1$-$C_6$ alkyl)

or R—O—CO— where R=t-butyl, Ar-alkyl (e.g. benzyl), 2,2,2-trichloroethyl or $R^6$—$SO_2$— where $R^6$=Ar (e.g. Ph, α-naphthyl, β-naphthyl) or other lipophilic group or one or more amino acyl residues either as such or in protected form bearing a group X above Y=absent, or glycine, or D- or L-phenylalanine or other lipophilic amino acid residue (e.g. Phg, Cha, α-Nal, β-Nal, p-iodophenylalanyl)

Z=L- or D-proline or a ring homologue (e.g. azetidine-2-carboxylic acid, piperidine-2-carboxylic acid) or L- or D-valine or N-methyl-alanine or glycine or Y and Z are as:

$$Y\overset{R}{\underset{X}{-}}Z$$

where the peptide bond —CO—NH— between Y and Z has been reduced (and protected) to give —$CH_2$—N(X)—, X being a protective group as defined above

A=

$$-NH-\underset{*}{CH}-\underset{\underset{O}{\overset{\|}{C}}}{}-CH_2-\underset{*}{CH}-CO- \qquad (1)$$

'keto' isostere (II)

-continued $$-NH-\underset{*}{CH}-\underset{\underset{OH}{|}}{\overset{R^1}{|}}-CH_2-\underset{*}{CH}-CO- \qquad (2)$$

'hydroxy' isostere (III)

$$-NH-\underset{*}{\overset{R^1}{CH}}-CH_2-\overset{R^3}{N}-\underset{*}{\overset{R^2}{CH}}-CO- \qquad (3)$$

'reduced' isostere (IV)

where:

(1)

$R^1 = -(CH_2)_n-NH-\underset{\underset{NH}{\|}}{C}-NH_2$ with n = 2-4 or $-(CH_2)_m-\phenyl-\underset{\underset{}{}}{\overset{NH}{\|}}{C}-NH_2$ or $-(CH_2)_m-\phenyl$ with $\underset{\underset{}{}}{\overset{NH}{\|}}{C}-NH_2$ where m = 0-2

(ii) $R^2$=H, lower alkyl ($C_1$-$C_4$) or 1-hydroxyethyl,
(iii) $R^3$=any one of groups X as defined above
(iv) configuration at the asymmetric centres * is either R or S Arg or Pro and Arg may be absent, Pro may be in substituted form (e.g. hydroxy-proline) and Arg may be in substituted form (e.g. with $Z^1$, Tos or —$NO_2$)

B=D or L-valine or D or L-proline or —NH—$(CH_2)_n$—CO—, where n=0-5, or absent

W=—OH as such or in protected form including —$OR^4$, where $R^4$=lower alkyl ($C_1$-$C_5$) or —$NH_2$ as such or in protected form including —$NHR^5$ or —$NR_2^5$ where $R^5$=lower alkyl ($C_1$-$C_5$) or $R_2^5$=cycloalkyl —$(CH_2)_n$— with n=3-5 where the ring is optionally substituted with carboxyl —COOH and/or alkyl ($C_1$-$C_5$) group(s)

B-W represents an aminoalcohol derivative of B as such or in protected form, or a residue in which one or more further amino acyl groups are present and where further in said compounds of formula I (especially those equivalent to a hexapeptide) the two terminals are optionally linked by a peptide bond to form a cyclic structure.

Particularly in general formula I above the following may apply:

X=H, lower alkyl ($C_1$-$C_5$) or other protecting group e.g. lower acyl ($C_1$-$C_5$) or R—O—CO— where R=t-butyl, benzyl, 2,2,2-trichloroethyl, or an amino acyl residue either as such or in a protected form Y=D- or L-phenylalanine, or glycine
Z=L- or D-proline, or L- or D-valine
In A:

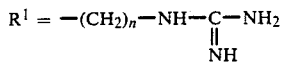

with n=2, 3 or 4

R² = H, methyl, isopropyl, sec-butyl, iso-butyl or 1-hydroxy-ethyl

R³ = H, lower aliphatic acyl $C_1$-$C_5$ or lower alkyl $C_1$-$C_5$, or R—O—CO— as for X configuration at the asymmetric centres * is either R or S Pro and Arg, or Arg alone, may be absent, or in substituted form e.g. OH for Pro, o, $Z^1$ (benzyloxycarbonyl) or $NO_2$ for Arg B = D- or L-valine, or D- or L-proline, or absent W =
—OH, or
—OR⁴ where R⁴ = lower alkyl $C_1$-$C_5$, or
—$NH_2$, or
—NHR⁵ or $NR_2^5$ where R⁵ = lower alkyl ($C_1$-$C_5$) or
$R_2^5$ = lower cycloalkyl —$(CH_2)_n$— with n=3, 4 or 5

Such peptide analogue may further be in the above form or may be modified by isosteric replacement of one or more remaining peptide bonds by keto —CO—$CH_2$—, hydroxy —CH(OH)—$CH_2$— or reduced —$CH_2$—NH— linkages, and may be in the free form or in a protected form at one or more remaining functional groups e.g. amino, imino or amide (including peptide) nitrogen, carboxyl, hydroxyl, guanidino. In particular, the analogues may be present in the form of their physiologically acceptable acid addition salts or other derivatives convertible in the body to the active compound (as shown by their effect). Such physiologically acceptable derivatives are included within the definition of the compounds in the description and claims herein.

Protective or substituent groupings may be any of those known in the polypeptide art, amply disclosed in the literature and not requiring discussion here. Generally the selection of the groups is according to their function, some being primarily intended to protect against undesired reaction during synthetic procedures while the N— and C— terminal substituents are for example directed against the attack of exopeptidases on the final compounds or to increase their solubility or lipophilicity and hence physiological acceptability. All these functions are generally within the term "protective group" or the like used in the description and claims herein.

The invention further extends to the use of the above described thrombin inhibitors in the prophylaxis or treatment of diseases associated with undesirable thrombogenesis.

EXAMPLES

The following detailed Examples illustrate the invention, the text of the examples being followed by tabulated reaction schemes. Examples I to VI are given in detail, followed by more abbreviated Examples VII to XVI on the same lines.

EXAMPLE I

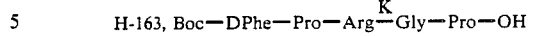

The synthesis of H-163 was carried out according to Scheme I. Arabic numerals underlined (e.g. 1) refer to structures in these Schemes. Arabic numerals in parentheses, e.g. (1) refer to reaction steps.

(1) $N^G$-Formyl-$N^G,N^G$-di(benzyloxycarbonyl)-L-arginine 1 was obtained from $N^G$-formyl-L-arginine by the method of Smithwick and Shuman (J. Org. Chem. 1974.39.3441) in 62% yield, or by the formylation of H—Arg($Z_2$)—$O^-K^+$ with formic-pivalic anhydride (60%).

(2) Oxazolone 2. HCO—Arg($Z_2$)—OH (1 mmol) was dissolved in dry THF—$CH_2Cl_2$ (1:5) and cyclised by treatment with DPECl.HCl salt (1.1 mmol) at 0° for 2 hrs. The oxazolone 2 was isolated as a pale yellow oil.

(3) (4) and (5). The oxazolone 2 (1 mmol) in dry THF at 0° was acylated with the succinic hemiester chloride 3 (1.1 mmol) in the presence of (1.2 mmol). The reaction mixture was stirred at 22° for 2 hrs, evaporated, the residue dissolved in pyridine and treated with DMAP (20 mg) at 22° for 90 mins. AcOH (2.5 ml) was added and the red solution was left at 22° for 16 hrs. After evaporation, and extraction of the crude product with ethyl acetate, chromatography on silica with EtOAc-petrol yielded the pure trichloroethyl ester 6 as a colorless oil (from 1)

(6) The trichloroethyl ester group was removed from (1.2 mmol) by treatment at 0° in THF (25 ml) with Zn powder (2.4 g) and cold 1M $NaH_2PO_4$ (6.5 ml) for 2½ hrs. The crude product was extracted with EtOAc and crystallized from EtOAc-petrol to give pure HCO—Arg($Z_2$)—$^K$Gly—OH, 7 (82%).

(7) The protected keto isosters 7 (0.189 mmol) was converted into its Pfp ester by treatment with Pfp-OH (0.2 mmol) and DCCI (0.19 mmol) in $CH_2Cl_2$ (2 ml) at 0° for 1½ hrs. This Pfp ester was coupled at 0° to H-Pro-OMe. HCl salt (1.1 mmol) in DMF containing $^iPr_2$NEt (2.5 equivalents). Chromatography of the crude product in EtOAc on silica yielded pure HCO-Arg($Z_2$)$^K$-Gly-Pro-OMe 8 (80%) as a colorless oil.

(8) (9) The formyl protecting group of 8 (0.13 mmol) was removed by treatment with 1M HCl/MeOH (30 ml) at 22° for 16 hrs. Evaporation yielded H-Arg($Z_2$)$^K$-Gly-Pro-OMe.HCl, 9 which was dissolved in DMF and coupled with Boc-DPhe-Pro-OPfp 11 (0.144 mmol) at 0° in the presence of $^iPr_2$NEt (0.27 mmol). The crude methyl ester 12 thus formed was purified by chromatography on silica in EtOAc and obtained as a colorless oil (70%).

(10) (11) The methyl ester 12 (0.04 mmol) in MeOH (0.9 ml) was treated will 1M KOH (0.1 ml) for 1½ hrs at 22° to remove the ester group and one of the Z protecting groups. The crude product was purified by hplc on Lichroprep RP18 in a gradient of MeOH and 5% AcOH to give the pure peptide acid 13 (26 mg). The latter was dissolved in MeOH—AcOH—$H_2O$ (5:1:1) and hydrogenates over 5% Pd/C to yield pure M-163. Tlc and hplc show the presence of two epimers. Tlc on silica in CHCl₃—MeOH-AcOH (6:1:1) $R_F$ 0.19 and 0.22. After hydrolysis at 110°/18 hrs with 6N HCl, amino acid analysis: Pro, 8.0, Pho, 0.99.

EXAMPLE II

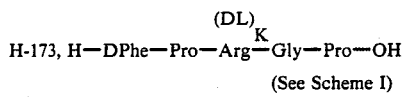
H-173, H—DPhe—Pro—Arg$\overset{\text{(DL)}}{\overset{\text{K}}{-}}$Gly—Pro—OH (See Scheme I)

*Trade Mark

(12) The $N^\alpha$-Boc-protected peptide H-163 was treated with aqueous 2M HCl for 2 hrs at 22°. The resulting deprotected peptide H-173 was obtained by lyophilisation. Analysis: Pro, 2.05, Phe, 0.95.

EXAMPLE III

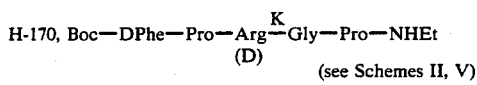
H-170, Boc—DPhe—Pro—Arg$\overset{\text{K}}{\underset{\text{(D)}}{-}}$Gly—Pro—NHEt (see Schemes II, V)

(1) The protected keto isostere 7 (0.189 mmol) was converted into its Pfp ester and coupled to H-Pro-NHEt (1.1 equivalents) in the same manner as described for the methyl ester in Example I step (7), to give the ethylamide 15 in 95% yield.

(2)(3) The formyl protecting group was removed from 15 by treatment with 1M HCl/MeOH and the resulting $N^\alpha$-deprotected peptide amide 16 was acylated with the Pfp ester 11 as described in sections (8) and (9) of Example I, to give a mixture of the epimers 17a and 17b (136 mg,75A).

(4) The latter were separated by chromatography on silica in 5% MeOH-EtOAc, yielding 56 mg of the faster moving epimer 17a ($R_F$ 0.35 on a silica tlc plate in MeOH-EtOAc 1:10) and 60 mg of the slower one 17b ($R_F$ 0.30). Synthesis of 17 by an independent route which preserves optical integrity at the carbon atom of L-arginine (see Scheme V) gave the slow moving epimer 17b, thus enabling assignment of configuration in the epimers 17a (fast moving, contains D-arginine) and 17b (slow-moving, contains L-arginine). Hydrogenolysis 17a over 5% Pd/C yielded the Boc-protected pentapeptide ethylamine H-170. Tlc on silica in CHCl₃-MeOH-AcOH (6:21:1) $R_F$ 0.39. Amino acid analysis after hydrolysis at 110°/18 hrs. with 6N HCl: Pro 2.04; Phe 0.96.

EXAMPLE IV

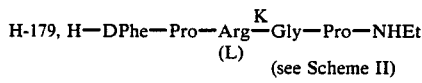
H-179, H—DPhe—Pro—Arg$\overset{\text{K}}{\underset{\text{(L)}}{-}}$Gly—Pro—NHEt (see Scheme II)

(4) Hydrogenolysis of the slow moving epimer 17b, obtained in step (3) of the synthesis of H-170, produced the Boc-pentapeptide amide H-171. The latter was treated with 2N HCl at 22° for 2 hrs and lyophilised to yield H-179.

Tlc on silica in CHCl₃-MeOH-AcOH (6:2:1) $R_F$ 0.15.
Amino acid analysis: Pro, 2.00; Phe 1.00

EXAMPLE V

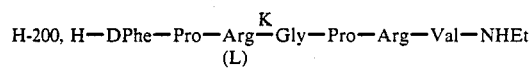
H-200, H—DPhe—Pro—Arg$\overset{\text{K}}{\underset{\text{(L)}}{-}}$Gly—Pro—Arg—Val—NHEt The synthesis of this compound was carried out according to Scheme III.

(1) H-Val-NHEt.HCl (3 mmol) in CH₂Cl₂ at 0°, was acylated with Boc-Arg(Z₂)-OPfp (2 mmol) in the presence of ⁱPr₂NEt (2 mmol) to yield, after a standard workup, the protected dipeptide ethylamide 25 (98%).

(2)(3) 25 (1.87 mmol) was deprotected by treatment with HCl/EtOAc and acylated with Boc-Pro-OPfp (3 mmol) in DMF at 0° in the presence of ⁱPr₂NEt (1.87 mmol). Standard workup procedure gave the protected tripeptide ethylamide 27 (80%).

(4)(5) 27 (0.587 mmol) was deprotected with HCl/EtOAc and reacted in DMF solution at 0° in the presence of ⁱPr₂NEt with the Pfp ester 28 (prepared from 7 with DCCI) to give the protected pentapeptide ethylamide 19 (95%).

(6)(7) 30 (0.17 mmol) was deformulated with 1N HOE/MeOH and the hydrochloride salt 31 was isolated by evaporation and drying over KOH pellets. It was then reacted in DMF at 0° with the Pfp ester 11 in the presence of ⁱPr₂NEt (2 equivalents). A mixture of epimers 32a and 32b was isolated from the reaction by standard procedures.

(8)(9) Epimers 32a and 32b were separated by chromatography on silica in MeOH-EtOAc (1:40) and the L-epimer 32a was hydrogenated in MeOH-AcOH-H₂O (5:1:1) over 5% Pd/C to give the Boc-protected heptapeptide ethylamide 33a.

(10) 33a was treated with 2N HCl at 22° for 2 hrs. Lyophilisation yielded pure H-200.Tlc on silica: $R_F$ 0.10 in CHCl₃-MeOH-AcOH (6:2:1). Analysis: Arg 1.10, Fbe 0.99; Pro 2.07; Val 0.83.

EXAMPLE VI

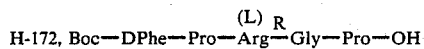
H-172, Boc—DPhe—Pro—Arg$\overset{\text{(L)}}{\overset{\text{R}}{-}}$Gly—Pro—OH This compound was prepared acccording to Scheme IV.

(1) Synthesis of Boc-Arg(Z₂)-H 18 was carried out according to the method of A. Ito et al., (Chem. Pharm. Bull. 1975.23.3081.) by reduction of Boc-Arg(Z₂)-OMe with di-isobutyl-aluminium hydride (ⁱBu₂AlH) in toluene. The pure aldehyde 18 was obtained after purification by rapid chromatography on silica in 50% yield.

(2) Preparation of H-Gly-Pro-OBzl, 19. Boc-Gly-OH was coupled via the mixed anhydride (prepared with isobutyl chloroformate and NMM), to proline benzyl ester. The resulting Boc-Gly-Pro-OBzl was treated with HCl/EtOAc to remove the Boc group and the HCl salt of 19 thus formed was used in the reductive alkylation step (3).

(3) Boc-Arg(Z₂)-$^R$Gly Pro-OBzl, 20. The aldehyde 18 (3 mmol) and H-Gly-Pro-OBzl 19 (3 mmol, obtained free the HCl salt with NMM) in dry THF, were allowed to react in this presence of 5 Å molecular sieve (10 g) at −10° for 5 hrs. The Schiff's base thus formed was reduced with Na CNBH₃ (3 moles) in methanol at −10°. Pure product 20 was isolated in 44% yield by chromatography in EtOAc on silica.

(4) 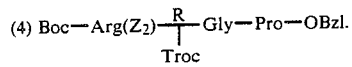 21

The reduced peptide 20 (0.6 mmol) in THF (40 ml) was acylated with 2,2,2-trichloroethoxycarbonyl chloride (Troc-Cl, 0.7 mmol) in the presence of NMM (0.7 mmol) at −15°. Silica gel chromatography of the crude product in EtoAc gave pure 21 in 58% yield.

(5) 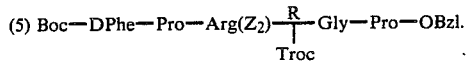 23

The protected reduced tripeptide 21 was treated with HCl/EtOAc to remove the Boc protecting group and the resulting N-deprotected compound 22 (0.32 mmol) was acylated with Boc-DPhe-Pro-OPfp (0.32 mmol) in dry DMF in the presence of $^i$Pr$_2$NEt (0.32 mmol). Silica chromatography of the crude product in EtOAc-benzene, produced pure 23 (45%).

(6) Removal of the Troc group from 23 to give intermediate 24. The fully protected reduced pentapeptide 23 (0.03 mmol) was dissolved in glacial acetic acid (0.8 ml) and treated with zinc powder (0.6 mmol in an atmosphere of nitrogen for 3 hrs. Chromatography of the crude product on silica gave pure 24 in 47% yield.

(7) Preparation of H-172. 24 obtained in step (6) was dissolved in a mixture of MeOH-AcOH-H$_2$O (5:1:1) and hydrogenated over 5% Pd/C for 3 hrs. Hplc of the crude product on Partisil ™ 10 ODS II in 64% MeOH-H$_2$O containing 0.2% formic acid gave pure H-172. Tlc in EtOAc-Py-AcOH-H$_2$O (30:20:6:11) R$_F$=0.25 on silica. After hydrolysis at 110°/18 hours with 6N HCl: Found Phe 0.96, Pro 2.04.

EXAMPLE VII

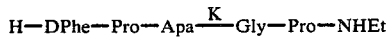 40

2-(4$^1$-Amidinophenyl)-alanine (Apa) was prepared by an adaptation of the method of G. Wagner et al (Pharmazie, 1981.36.597) and was converted into the ωN-benzyloxycarbonyl-αN-formyl derivative by standard methods. The latter was subjected to the sequence of reactions described for the corresponding arginine derivative in Schemes I and II to yield compound 40. Alternatively the reaction sequence may be carried out with 3- or 4-cyanophenylalanine and the side chain of the latter converted into the side chain of Apa or Amp at the end of the synthesis by the method of Wagner.

EXAMPLE VIII

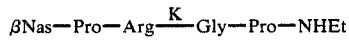 41

Naphthalene-2-sulphonyl chloride (βNas-Cl) was reacted with the sodium salt of L-proline under Schotten-Baumann conditions to yield βNas-Pro-OH. The latter was converted into the pentafluorophenyl ester and reacted with the partially protected tripeptide analogue 16. (Scheme II) to give compound 41.

EXAMPLE IX

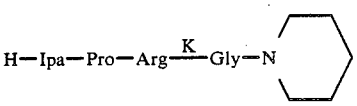 42 t-Butyloxycarbonyl-4-L-iodophenylalanine(Boc-Ipa-OH) was coupled to L-proline sodium salt via the pentafluorophenyl active ester, and the resulting Boc-Ipa-Pro-OH was then coupled to H-Arg(Z$_2$)-$^K$Gly-piperidide. The L-epimer of the product (at the Arg α-carbon) was separated by chromatography and deprotected, first by hydrogenolysis in the presence of palladium on charcoal, and then by treatment with 2M HCl to yield compound 42.

EXAMPLE X

 43

L-Proline was N-acylated with phenoxyacetyl chloride and the acyl compound coupled, via its pentafluorophenyl ester, to compound 16 (Scheme II) as described in Example VIII.

EXAMPLE XI

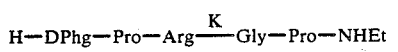 44

This compound was prepared according to the method described in Scheme II for Example IV, except that t-butyloxycarbonyl-D-phenylglycine pentafluorophenyl ester (Boc-DPhg-OPfp) was used in place of Boc-DPhe-OPfp.

EXAMPLE XII

 45

This analogue was synthesised according to the method described in Scheme VI.

EXAMPLE XIII

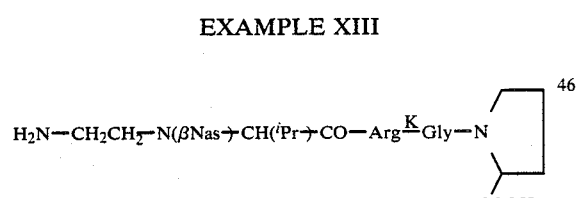 46

The above compound was synthesised according to Scheme VII.

EXAMPLE XIV

 47

The synthesis of this cycle peptide analogue is shown in Scheme VIII.

EXAMPLE XV

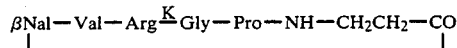

The preparation of this cyclic peptide analogue is described in Scheme IX.

EXAMPLE XVI

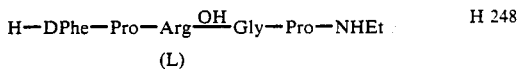     H 248

The above analogue, which is believed to be in the S configuration at the carbon atom bearing the hydroxyl group is prepared from the compound H 179 of Example IV by reduction of the keto group with sodium cyanoborohydride and separation of the resulting mixture of R and S epimers.

SYNTHESIS SCHEMES

The synthesis schemes referred to above now follow.

SCHEME I (Examples 1, 2, 7)

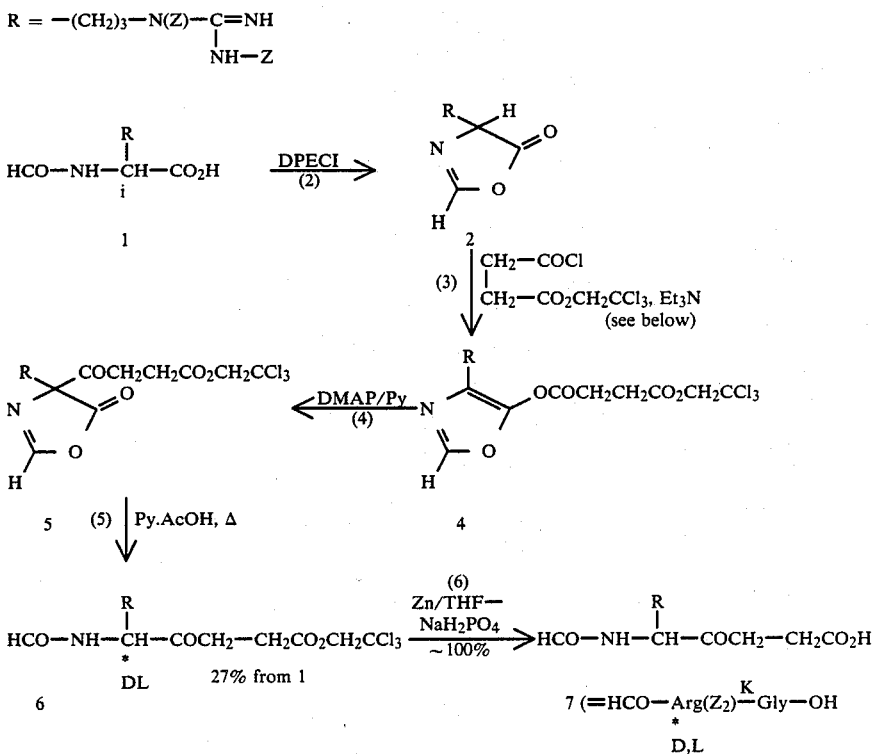

Synthesis of 3

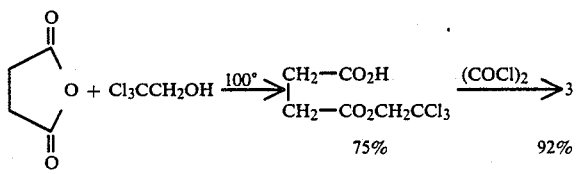

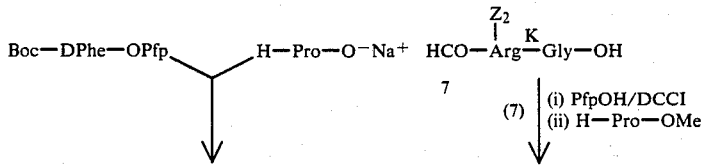

-continued
SCHEME I (Examples 1, 2, 7)
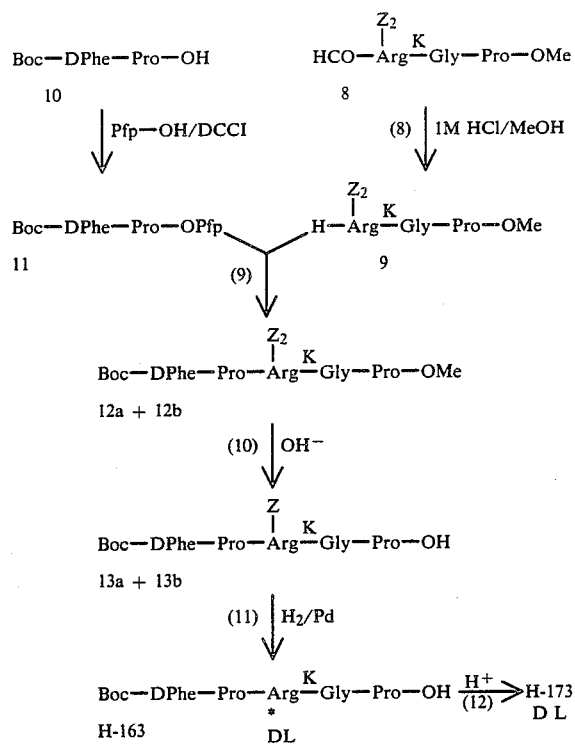
SCHEME II (Examples 3, 4, 7, 8, 10, 11)
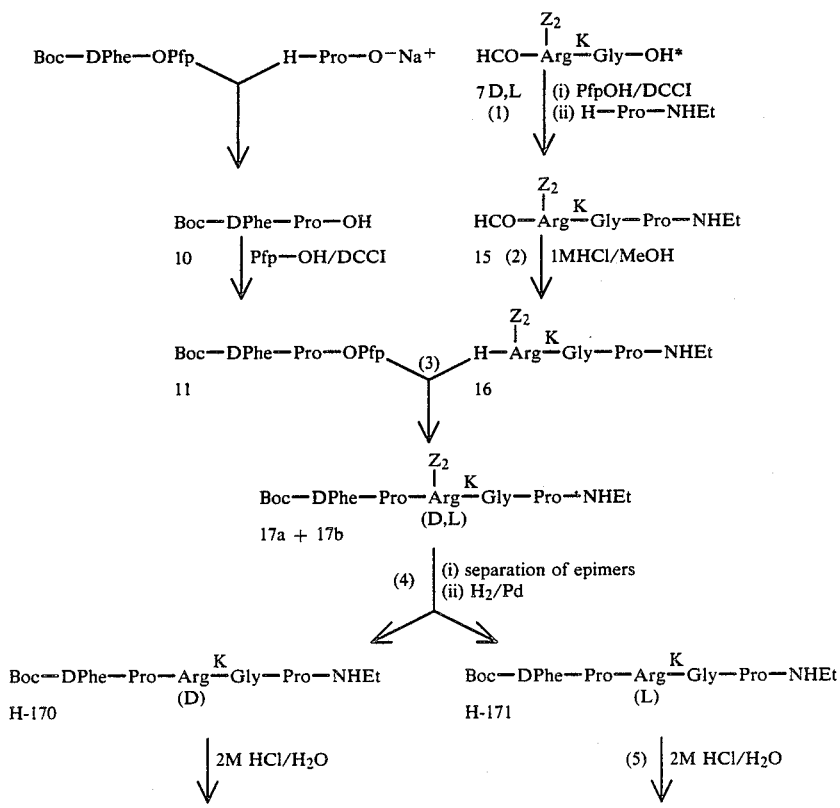

-continued
SCHEME II (Examples 3, 4, 7, 8, 10, 11)
SCHEME III
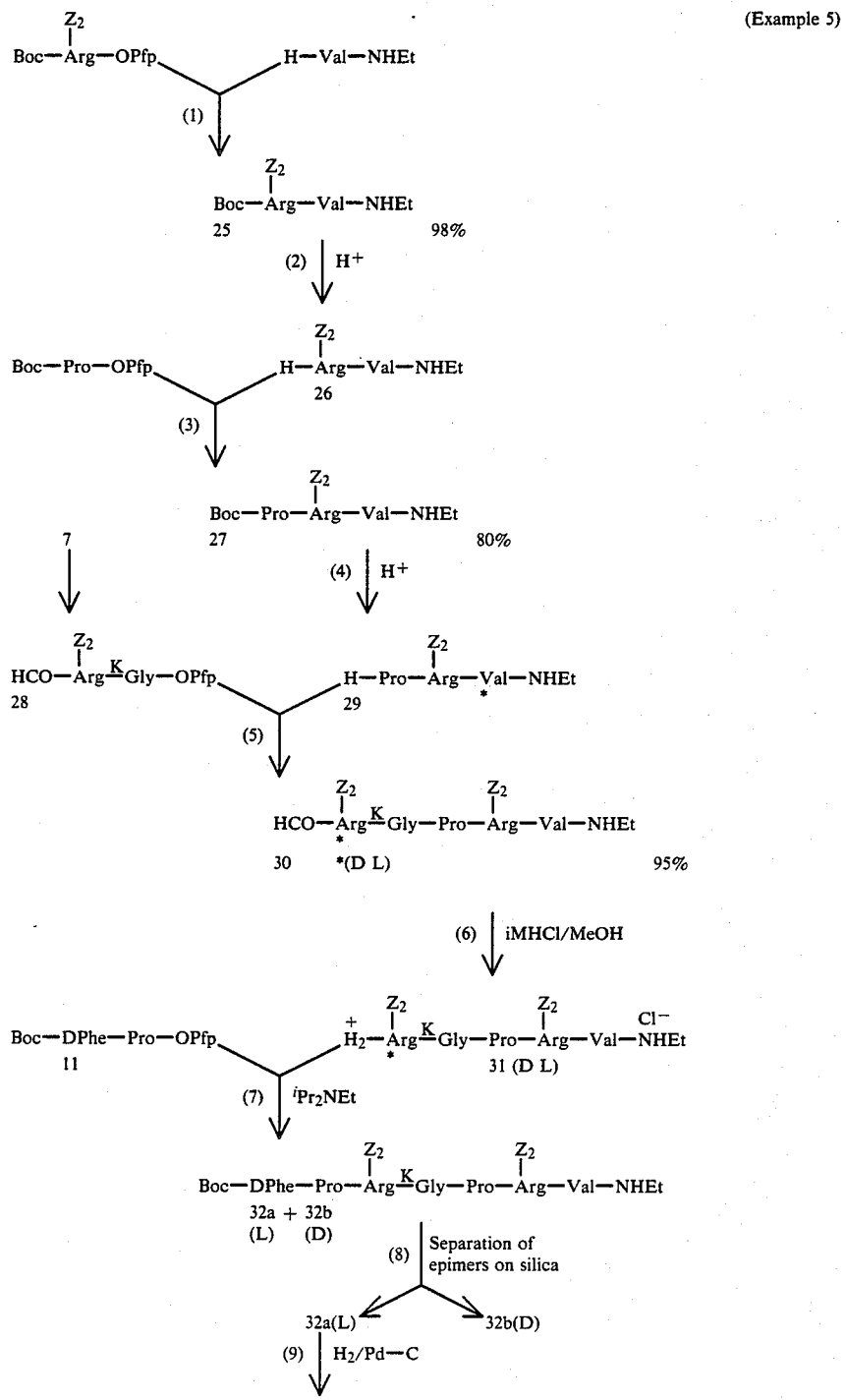

SCHEME III
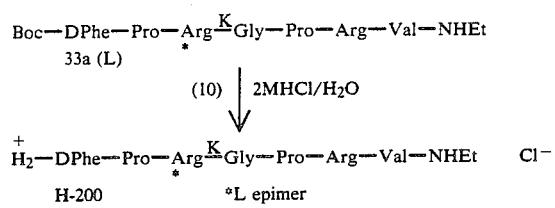
SCHEME IV
(Example 6)
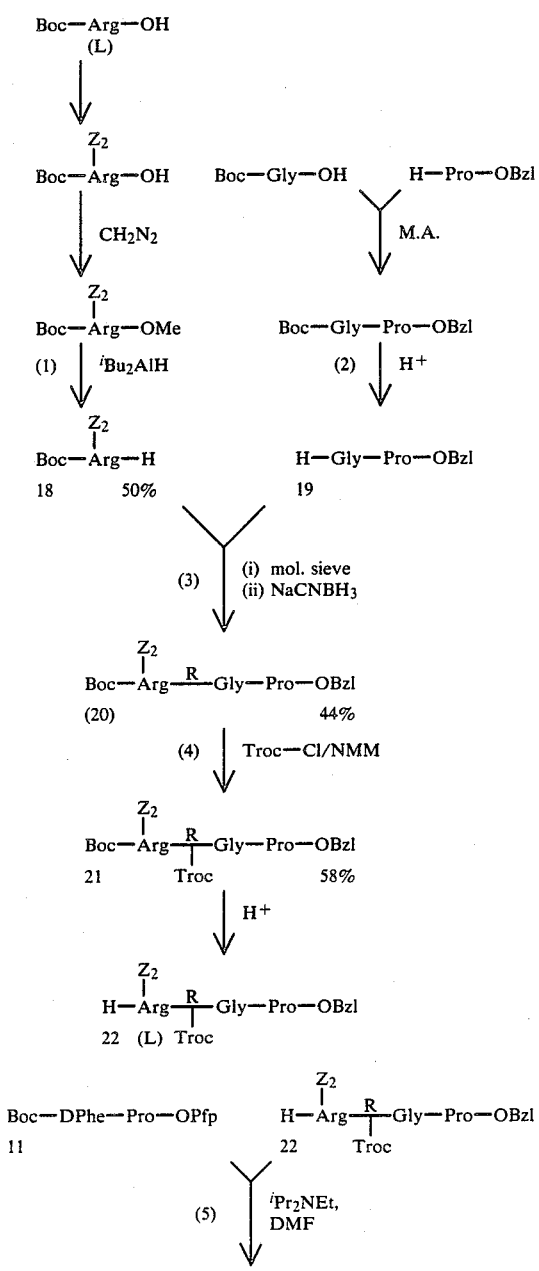
-continued
SCHEME IV
(Example 6)
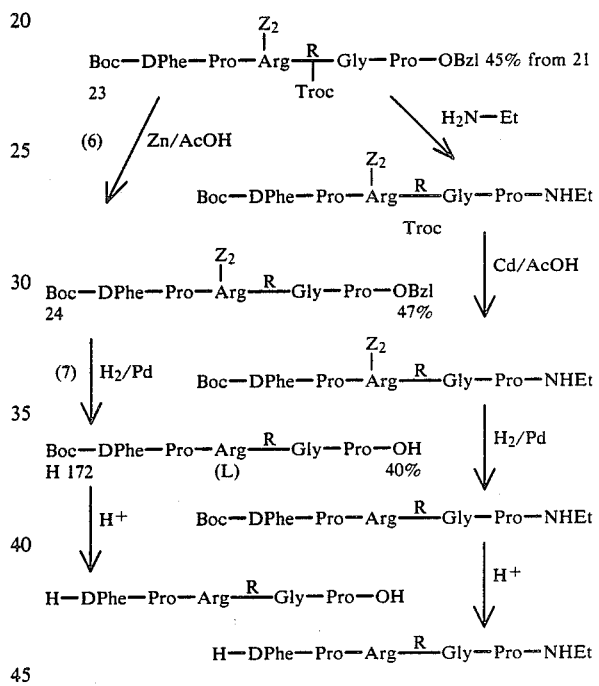
SCHEME V
(Example 3)
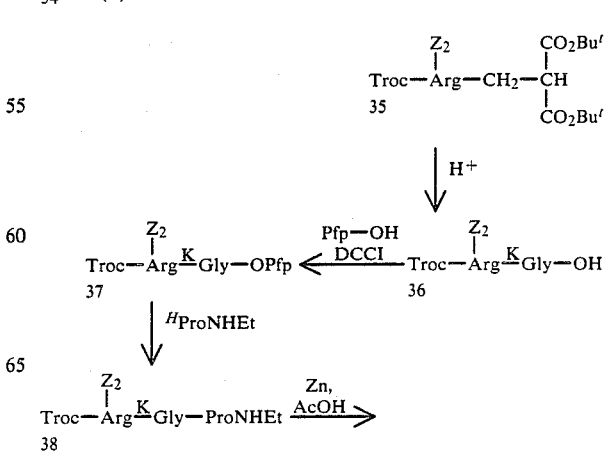

-continued
SCHEME V
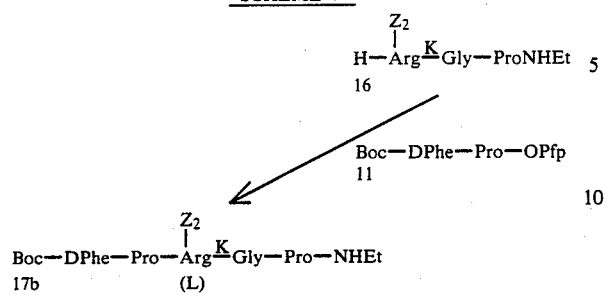
Scheme VI
(Example 12)
Synthesis of compound 45
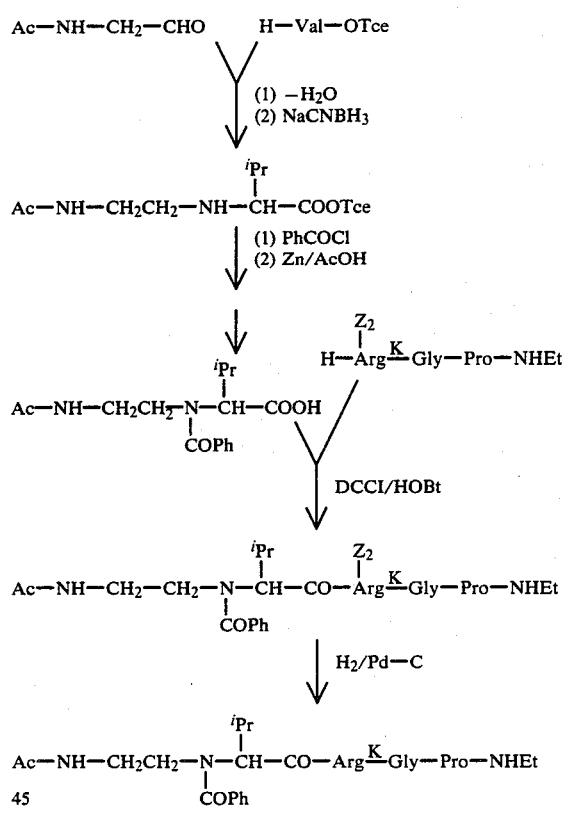
Scheme VII (Example 13)
Synthesis of compound 46
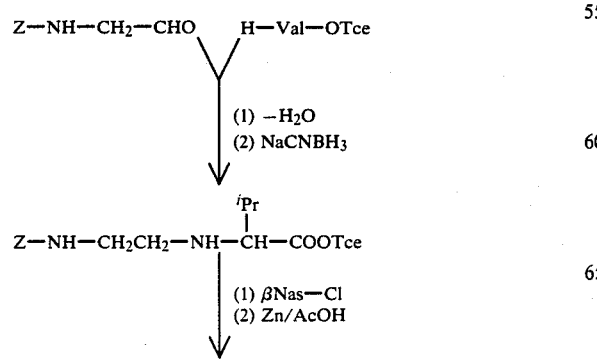
Scheme VII (Example 13)
Synthesis of compound 46
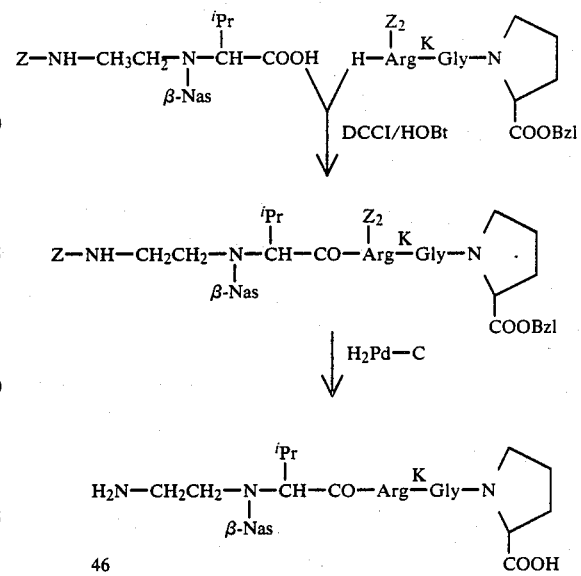
Scheme VIII (Example 14)
Synthesis of compound 47
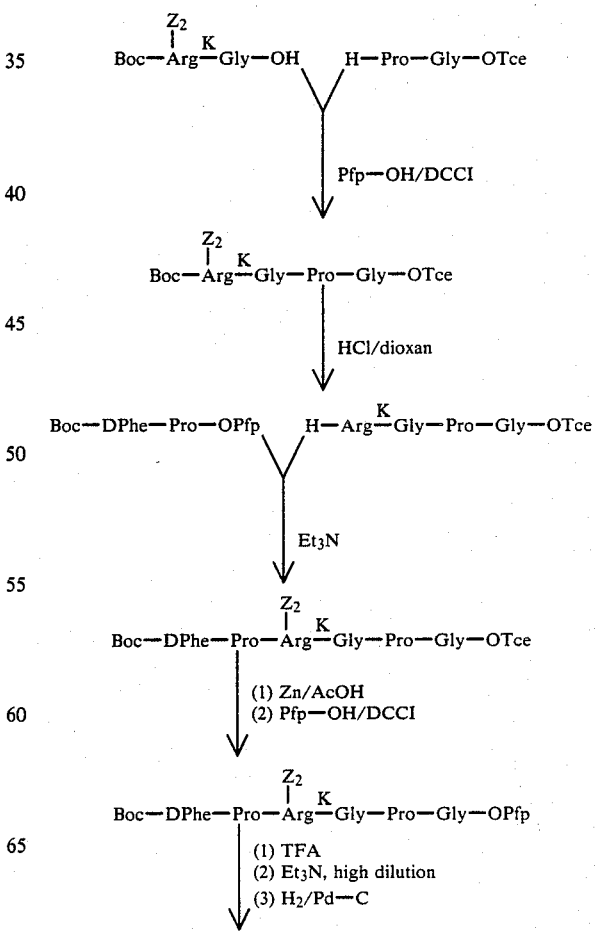

-continued
Scheme VIII (Example 14)
Synthesis of compound 47

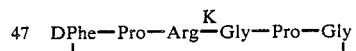

47  DPhe—Pro—Arg$\overset{K}{-}$Gly—Pro—Gly

Scheme IX (Example 15)
Synthesis of compound 48

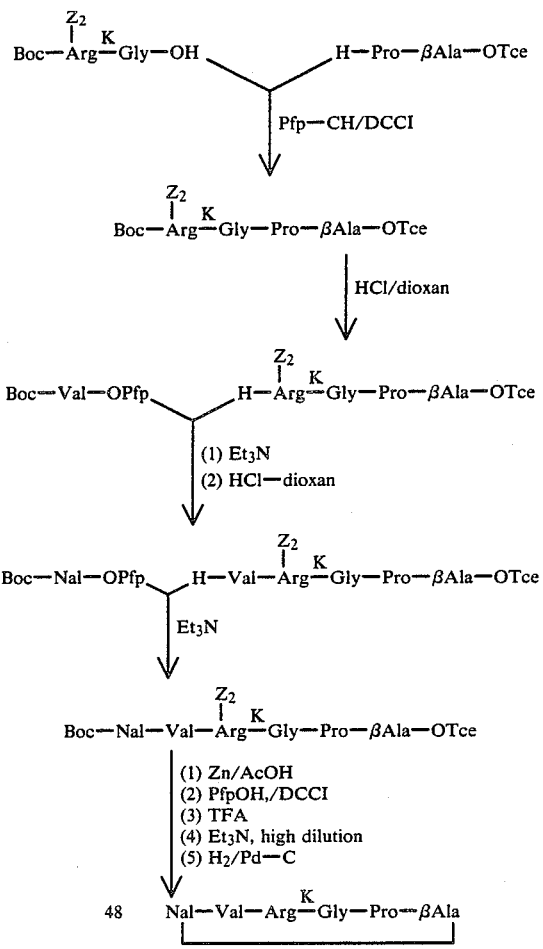

48  Nal—Val—Arg$\overset{K}{-}$Gly—Pro—βAla

BIOLOGICAL ACTIVITY

Compounds were tested in vitro for the following activities, using standard procedures:

(a) Inhibition of human thrombin hydrolysing the chromogenic substrate S-2238 (for details of the method, see M. F. Scully and V. V. Kakkar, Clin. Chim. Acta 1977.79.595). Series of measurements were carried out using a number of different inhibitor concentrations and at least two different substrate concentrations. The inhibitory constant $K_1$ was determined graphically, using a Dixon plot (M. Dixon, Biochem. J. 1953.55.170)

(b) Prolongation of kaolin-cephalin clotting time (KCCT; for method see D. E. G. Austen and I. L. Rhymes: "Laboratory Manual of Blood Coagulation", Blackwell, Oxford 1975). Results have been expressed as the molar concentration of inhibitor required to double the KCCT.

(c) Inhibition of thrombin-induced platelet aggregation (for method see G. V. R. Born, Nature 1962.194 927).

Representative results for Examples I-VI are shown in the Table.

TABLE

| Code No | Example No | $K_1$ for human thrombin (μM) | Conc. to double KCCT (μM) | $K_1$ for thrombin induced platelet aggregation (μM) |
|---|---|---|---|---|
| H-163 | I | 120 | 226 | |
| H-170 | III | 68 | 21 | 0.3 |
| H-172 | VI | 112 | 813 | |
| H-173 | II | 30 | 28 | |
| H-179 | IV | 6 | 15 | 0.4 |
| H-200 | V | 3 | | |

Some of the compounds described in this specification have been tested in vivo for their ability to prolong clotting time and have shown marked activity. These tests were carried out in rabbits, using between 0.1-4 mg/Kg of the inhibitor and comparing the KCCT or the thrombin clotting time in blood samples taken before and at various time intervals after the administration of inhibitors. H 179 for example prolongs thrombin clotting time from 25 to 220 seconds at 2.35 mg/Kg and from 25 to 280 seconds at 4.7 mg/Kg, and is comparable to heparin both in potency and in its in vivo half life in plasma (18 minutes; heparin 15 minutes).

USE IN TREATMENT

As noted earlier herein the compounds of the invention may be used in prophylaxis against or treatment of diseases associated with undesirable thrombogenesis, in place for example of the well known use of heparin. Dosages vary according to the potency of the inhibitor and the degree of effect required, and their frequency on the life of the inhibitor in the body, but are likely to be in the range 0.01 to 10 mg/Kg for example as dosage units of 0.75 mg to 0.75 g. Specifically for example the compound H 179 may be given in 1 mg doses either parenterally or by the oral route.

| Abbreviations used | |
|---|---|
| AcOH | Acetic Acid |
| Boc | t-Butyloxycarbonyl |
| $^i$Bu$_2$AlH | Di-isobutyl aluminium hydride |
| Bzl | Benzyl |
| DCCI | N,N'—Dicyclohexyl carbodiimide |
| DCU | N,N'—Dicyclohexylurea |
| DMAP | 4-Dimethylamino-pyridine |
| DMF | Dimethylformamide |
| DPECI | N—dimethylaminopropyl-N'—ethyl-carbodiimide |
| Et$_3$N | Triethylamine |
| EtOAc | Ethyl acetate |
| hplc | high performance liquid chromatography |
| K | Keto isostere —COCH$_2$— |
| M.A. | Mixed anhydride |
| MeOH | Methanol |
| NMM | N—methylmorpholine |
| nmr | nuclear magnetic resonance |
| Petrol | Petroleum ether 60-80° |
| Pfp | Pentafluorophenyl |
| $^i$Pr$_2$NEt | Di-isopropyl-ethylamine |
| Py | Pyridine |
| R | Reduced isostere —CH$_2$—NH— |
| tlc | thin layer chromatography |
| Troc | 2,2,2-Trichloroethoxycarbonyl |
| Z$^1$ | Benzyloxycarbonyl (simply as Z in the examples) |
| Amp | 3-(3'-Amidinophenyl)-alanine |
| Apa | 3-(4'-Amidinophenyl)-alanine |

| Abbreviations used | |
|---|---|
| Ar | Aryl: aromatic group, mono- or bicyclic |
| Cha | 3-Cyclohexyl-alanine |
| HOBt | 1-Hydroxy-benzotriazole |
| αNal | 3-(1'-Naphthyl)-alanine |
| βNal | 3-(2'-Naphthyl)-alanine |
| Phg | 2-phenylglycine |
| TFA | Trifluoroacetic acid |
| Tce | 2,2,2-Trichloroethyl |
| Tos | Tosyl |
| THF | Tetrahydrofuran |
| hplc | High pressure liquid chromatography |
| β-Nas | Naphthalene-2-sulphonyl |
| Ipa | 4-Iodophenylalanine |

We claim:
1. Polypeptide analogues of the formula:

$$X-Y-Z-A-Pro-Arg-B-W \quad (I)$$
$$\phantom{X-Y-}14\phantom{-}15\,16,17\phantom{-A-}18\phantom{-}19\phantom{-}20$$

where
X=H or an N-protective group:
  F, Cl, Br, I, —CF$_3$, —OH, —OR or —R (R=C$_1$-C$_6$alkyl)
  or R—O—CO— where R=t-butyl, benzyl, 2,2,2-trichloroethyl
  or R$^6$—SO$_2$— where R$^6$=Ph, α-naphthyl β-naphthyl
  or one or more amino acyl residues as such or in N-protected form bearing a group X above;
Y=absent, or glycine,
  or D- or L-phenylalanine
  or a lipophilic amino acid residue selected from the group consisting of Phg, Cha, α-Nal, β-Nal and p-iodophenylalanyl;
Z=L- or D-proline or a ring homologue selected from the group consisting of azetidine-2-carboxylic acid and piperidine-2-carboxylic acid,
  or L- or D-valine,
  or N-methyl-alanine,
  or glycine;
or Y and Z are as:

where the peptide bond —CO—NH— between Y and Z has been reduced (and protected) to give —CH$_2$—N(X)—, X being a protective group as defined above;
A=

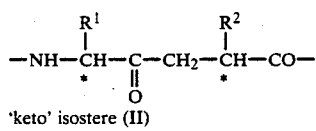
'keto' isostere (II)

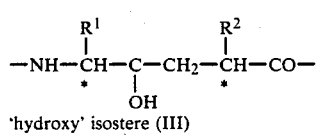
'hydroxy' isostere (III)

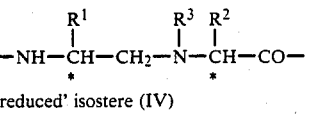
'reduced' isostere (IV)

where:
(i)

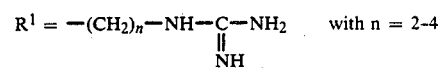

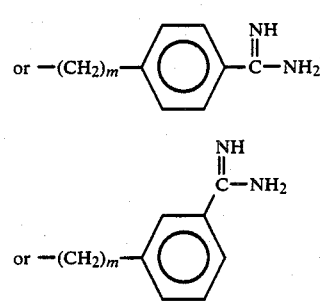

(ii) R$^2$=H, lower alkyl (C$_1$-C$_4$) or 1-hydroxy-ethyl,
(iii) R$^3$=a protective group as defined above;
(iv) configuration at the asymmetric centres* is either R or S
Arg or both Pro and Arg may be absent, Pro or Pro substituted with hydroxy-proline and Arg or Arg substituted with Z, Tos or —NO$_2$
B=D- or L-valine or
  D- or L-proline or
  —NH—(CH$_2$)$_n$—CO—, where n=0-5, or absent
W=(i) —OR$^4$, where R$^4$ is hydrogen or an O-protecting group; or (ii) —NHR$^5$ or —N(R$^5$)$_2$ where each R$^5$ is hydrogen
  or an N-protecting group; or (iii) a group with one or more further amino acyl residues
or B-W represents an aminoalcohol derivative of B as such or in protected form, and where further in said compounds of Formula I the two terminals are optionally linked by a peptide bond to form a cyclic structure.

2. Polypeptide analogues according to claim 1, wherein:
X=H or a protecting group:
  F, Cl, Br, I, —CF$_3$, —OH, —OR or —R (R=C$_1$-C$_6$alkyl)
  or R—O—CO— where R=t-butyl, benzyl, 2,2,2-trichloroethyl
  or R$^6$—SO$_2$— where R$^6$=Ph, α-naphthy; β-naphthyl of an amino acyl residue as such or in protected form bearing a group X above,
Y=D- or L-phenylalanine, or
  glycine,
Z=L- or D-proline, or
  L- or D-valine
In A:

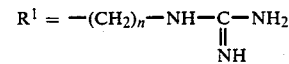

with n=2, 3 or 4

$R^2$=H, methyl, isopropyl, sec-butyl, iso-butyl or 1-hydroxy-ethyl $R^3$=H, lower aliphatic acyl $C_1$-$C_5$ or lower alkyl $C_1$-$C_5$, or t-butyl, benzyl, or 2,2,2-trichloroethyl configuration at the asymmetric centres* is either R or S B=D- or L-valine, or
D- or L-proline, or absent W=—OH, or
—$OR_4$ where $R_4$=lower alkyl $C_1$-$C_5$, or
—$NH_2$, or
—$NHR^5$ or $NR_2^5$ where $R^5$=lower alkyl ($C_1$-$C_5$) or alternatively $R_2^5$=lower cycloalkyl —$(CH_2)_n$— with n=3, 4 or 5.

3. Polypeptide analogues according to claim 1 wherein A is the 'keto' isostere (II).

4. Polypeptide analogues according to claim 1, modified by isosteric replacement of one or more remaining peptide bonds by 'keto' 'hydroxy' or 'reduced' isosteric links.

5. Polypeptide analogues according to claim 1, in protected form at one or more remaining amino, imino, amide (including peptide), guanidino, hydroxyl, carboxyl or other functional groups.

* * * * *